United States Patent
Shaw et al.

(10) Patent No.: US 7,312,073 B2
(45) Date of Patent: Dec. 25, 2007

(54) METHOD FOR THE DETECTION OF VIABLE MICROORGANISMS

(75) Inventors: Erich Shaw, Ashkelon (IL); Jean-Claude Robin, Enghien les Bains (FR)

(73) Assignee: BioGem Optical Ltd., Tel-Aviv (IL)

( * ) Notice: Subject to any disclaimer, the term of this patent is extended or adjusted under 35 U.S.C. 154(b) by 128 days.

(21) Appl. No.: 10/415,844

(22) PCT Filed: Nov. 8, 2001

(86) PCT No.: PCT/IL01/01040

§ 371 (c)(1),
(2), (4) Date: Jan. 12, 2004

(87) PCT Pub. No.: WO02/38724

PCT Pub. Date: May 16, 2002

(65) Prior Publication Data

US 2005/0202523 A1      Sep. 15, 2005

(30) Foreign Application Priority Data

Nov. 9, 2000   (IL) ................................ 139593

(51) Int. Cl.
- *C12M 1/34* (2006.01)
- *C12M 3/00* (2006.01)
- *C12M 1/22* (2006.01)
- *G01N 33/456* (2006.01)
- *G01N 33/552* (2006.01)

(52) U.S. Cl. ............... 435/288.7; 435/287.9; 435/808; 435/968; 435/305.1; 435/288.3; 436/535; 436/527; 436/811

(58) Field of Classification Search ............ 435/288.7, 435/287.9, 808, 968, 305.1, 288.3; 436/535, 436/527, 811

See application file for complete search history.

(56) References Cited

U.S. PATENT DOCUMENTS 5,272,240 A * 12/1993 Haruvy et al. ............... 528/10

(Continued)

FOREIGN PATENT DOCUMENTS

EP    0 439 318 B1    5/1998

(Continued)

OTHER PUBLICATIONS

Armon R., et al, Sol-Gel as Reaction Matrix for Bacterial Enzymatic Activity, Journal of Sol-Gel Science and Technology, vol. 19, No. 1/2/3, pp. 289-292, 2000.

(Continued)

*Primary Examiner*—Gladys J P Corcoran
*Assistant Examiner*—Nathan A. Bowers
(74) *Attorney, Agent, or Firm*—William J. Sapone; Coleman Sudol Sapone P.C.

(57) ABSTRACT

Method for the detection and enumeration of viable microorganisms. A liquid that comprises one or more markers incorporated in a liquid sol-gel precursor, is provided. A transparent slide is coated with a thin uniform layer of the liquid sol-gel precursor composition. The microorganisms are separated from liquid sample to be analyzed by passing the sample through a filter, and then bringing the filter into close contact with the sol-gel coated slide. The filter is co-incubated with the sol-gel coated slide for a period of time and at a temperature suitable to promote uptake of the markers by the microorganisms. The gel-coated slide irradiated with an external energy source, so as to generate detectable signals emitted from the markers uptaken by the microorganisms. Image of the detectable signals emitted from the microorganisms are acquired, and analyzed using a computer system, in order to provide the identification and enumeration of the microorganisms.

30 Claims, 3 Drawing Sheets

U.S. PATENT DOCUMENTS

| | | | |
|---|---|---|---|
| 5,681,712 A | * | 10/1997 | Nelson .................... 435/30 |
| 5,739,003 A | * | 4/1998 | Brocklehurst et al. ........ 435/29 |
| 5,861,270 A | * | 1/1999 | Nelis ....................... 435/34 |
| 6,022,748 A | * | 2/2000 | Charych et al. ............ 436/527 |
| 6,913,877 B1 | * | 7/2005 | Chaplen et al. ............... 435/4 |
| 2002/0192742 A1 | * | 12/2002 | Ushiyama et al. ........... 435/34 |

FOREIGN PATENT DOCUMENTS

| | | |
|---|---|---|
| WO | WO 96/14431 | 5/1996 |
| WO | WO 96/25665 | 8/1996 |
| WO | WO 99 10743 | 3/1999 |

OTHER PUBLICATIONS

Armon R., et al, Sol-Gel Applications in Environmental Biotechnology, Journal of Biotechnology, vol. 51, No. 3, pp. 279-285, Nov. 15, 1996).

Hong E., et al, Detection of Cryptosporidium Parvum in Antibody-doped Gels, Mater. Res. Soc. Symp. Proc., vol. 435, pp. 449-454, 1996.

\* cited by examiner

METHOD FOR THE DETECTION OF VIABLE MICROORGANISMS

FIELD OF THE INVENTION

The present invention is concerned with a method and compositions for the fast detection and enumeration of low concentration of viable microorganisms using organic or inorganic substances that are entrapped in porous sol-gel glass.

BACKGROUND OF THE INVENTION

A major goal of microorganism detection research is to develop inexpensive, fast, reliable, and sensitive detectors. Standard laboratory procedures are currently available for the detection of microorganisms. The vast majority of procedures are based on the use of agar media on which specific microorganisms grow over a period of time. The normal incubation period is between 24 to 48 hours. After the microorganisms multiply their presence can be identified and quantified.

The main drawback of the existing tests is the time required for obtaining their results. Bacterial contamination in water sources results in the shutdown of water sources and systems and requires the use of more expensive water supply alternatives. Fast detection of microorganisms is needed to allow for shorter shutdown periods. In the medical sector, bacterial identification and antibiotic sensitivity tests are required in any medical situation in which antibiotics are to be administrated. The time required for obtaining test results is between 72 to 96 hours. Reducing this time period will produce better results and faster patient recovery. In the food and beverage industry, raw materials and manufactured goods are routinely inspected for bacterial contamination. The required incubation period for test results does not allow for immediate process treatment and causes delays both in the manufacturing and supplying of goods. Reducing the taking time period can result in savings in infrastructure and labor.

In the last few years several methods were developed in order to identify and enumerate bacteria in 1.5 to 11.0 hours. Methods that are relatively simple require a large amount of bacteria (above $10^4$ in 1 ml sample), while methods that can detect small numbers of bacteria are expensive and cannot be used as large scale systems.

U.S. Pat. No. 5,811,251 discloses a system for counting the number of viable microorganisms based on a CCD system. However this system cannot differentiate between different types of bacteria and provides only a total number of bacteria. U.S. Pat. Nos. 5,972,641 and 5,518,894 disclose a rapid coliform detection systems using a statistic methods for determining the number of bacteria. Said methods require up to 11 hours for obtaining the results in low number of bacteria. Other patents disclose a method for detection of microorganisms using fluorescence and laser light source (U.S. Pat. Nos. 5,891,394, 5,858,697, 5,763, 203, 5,751,839 and 5,663,057). The disadvantages of said methods is the use of an expensive laser light source and the detection of microorganisms directly from the filter which is not smooth and causes problems during analysis. In addition, these systems are not portable and are relatively expensive.

Immunoassay methods are also used for detecting certain types of microorganisms (Lee et al., App. Environ. Microbiol., Vol. 56, pp.1541-1546). In these methods, specific antibodies labeled with a fluorescent or radioactive dye are used to detect the microorganism. However, immunoassay methods are limited in that they require the production of antibodies against each microorganism of interest, which is time-consuming and expensive.

"Sol-gel" is the term used to indicate inorganic glass manufactured at room temperatures based on metal oxides. A certain process involving ceramic materials in which the sol (solution) is transformed to a gel phase through hydrolysis, condensation and polymerization. The common starting materials for the sol-gel preparation are ormosils or metal oxides. In recent years sol-gel has been applied to organosilanes to create "glass at room temperature". Sol-gel type materials comprise pores ranging from tens of angstroms to tens of nanometers, and exhibit a large area to mass ratios e.g., hundreds of square meters per gram. Sol-gel materials are transparent even at UV wavelengths, and are simple to prepare in different shapes, such as powders, monolithic blocks, thin sheets, fibers etc.

The use of sol-gel-based materials to entrap various organic molecules in a matrix media was described in the art. (Avnir et al., Supramolecular architecture in two and three dimensions Bein T. (ed.) American Chemical Society Symposium Series XXX, 1992). Using said technology, organic molecules are entrapped at room temperatures within the sol-gel matrix without impairing the structure of the relatively sensitive organic molecule. In addition, the entrapped molecule retains almost all of the original physical and chemical characteristics, and is available to outside reactants as a result of the massive pore system inside the sol-gel.

U.S. Pat. No. 6,022,748 discloses a method for the direct detection of analytes using color changes in response to selective binding of analytes to a surface. Said detection occurs in immobilized biopolymeric material encapsulated into metal oxide glass using the sol-gel method. The disadvantages of this method are that only large amounts of bacteria can be detected or enumerated, since only high counts are able to cause a visible color change in the sol-gel. Furthermore, said method cannot differentiate between viable and non-viable microorganisms, since it is based on the binding of the microorganisms to the sol-gel surface, independent whether said microorganisms are viable or not.

Armon et al. (J. of Biotechnology 51, 279-285) disclose a method for detecting large quantities of *E. coli* bacteria by spreading them on sol-gel doped with specific compounds, said compounds being uptaken into the bacteria, which consequently causes the bacteria to glow at specific wavelengths. However, this method does not provide a method suitable to count bacteria present in a given sample. In addition, detection of low number of microorganisms is not possible using said method.

The art has so far failed to provide a fast method for the enumeration of microorganisms, which is sensitive enough to provide a reliable count at low microorganism concentrations.

It is a purpose of this invention to provide a fast and sensitive method for the detection of viable microorganisms.

It is another object of the invention to provide a method and compositions useful in providing an enumeration of microorganisms found in low-count samples.

Other objects and advantages of the invention will become apparent as the description proceeds.

SUMMARY OF THE INVENTION

It has now been surprisingly found, and this is an object of the present invention, that viable microorganisms at a concentration lower than $10^3$ ml$^{-1}$ may be detected and enumerated in a 2-hours period, using organic or inorganic substances that are entrapped in porous sol-gel glass (hereinafter referred to as "markers", for the sake of brevity).

The present invention relates to methods and compositions for the detection and enumeration of viable microorganisms using organic or inorganic substances that are incorporated in porous sol-gel glass (markers). The microorganisms metabolize said markers, and thereby emit detectable radiation, electromagnetism or fluorescence. Thus, a fast visualization of viable microorganisms is obtained on the sol-gel glass. The sol-gel surface is extremely smooth and transparent and allows for an almost uniform focal point for high resolution microscopic scanning.

According to a preferred embodiment of the invention, the following steps are carried out:
a) Providing a liquid composition comprising one or more marker(s) incorporated in a liquid sol-gel precursor;
b) Coating a transparent slide, e.g., a glass slide, with a thin uniform layer of said liquid sol-gel precursor composition;
c) Separating the microorganisms from a liquid sample to be analyzed by passing said sample through a filter, and then bringing said filter into close contact with the sol-gel-coated slide;
d) Co-incubating said filter with said sol-gel-coated slide for a period of time and at a temperature suitable to promote uptake of the marker(s) by the microorganisms, e.g. at 35-44° C. for 0.5 to 6 hours;
e) Irradiating said sol-gel-coated slide with an external energy source such as to generate detectable signals emitted from the marker(s) metabolized by the microorganisms; and
f) Acquiring images of said detectable signals emitted from the microorganisms, and analyzing said images using a computer system, thereby to provide the identification and enumeration of said microorganisms.

The present invention further relates to a method for preparation of a liquid sol-gel mixture containing organic or inorganic substances (markers). Said markers are metabolized by the microorganisms that are to be identified.

Coliform bacteria that can be detected according to the present invention are actually a broad group of bacteria that include *E. coli, Enterobacter* spp., *Klebsiella* spp. and *Citrobacter* spp. Coliform bacteria are identified by detecting the activity of an enzyme, β-Galactosidase (E.C. 3.2.1.23), using fluorogenic or chromogenic substances 3-carboxyumbelliferyl β-D-galactopyranoside (CUG) or 4-chloromethyl-6,8-difluoroumbelliferyl β-D-galactopyranoside (CMDi FUG).

According to the present invention, *E. coli* are identified by detecting the activity of an *E. coli*-specific-enzyme, β-Glucuronidase (GUS or EC 3.2.1.31), using the following fluorogenic or chromogenic substances: 4-methylumbelliferyl β-D-galactopyranoside (MUG), fluorescein di β-D-galactopyranoside (FDG), 6,8-difluoro-4-methylumbelliferyl β-D-glucuronide, lithium salt (DiFMUGGlcU), 2-dodecylresorufin, Elf-97, fluorescein di-β-glucoronide (FDGlcU), 5-(pentafluorobenzoylamino) fluorescein di-β-D-glucoronide (PFB-FDGlcU) and β-trifluoromethylumbelliferyl β-D-glucoronide.

According to another preferred embodiment of the invention, an antibiotic material is incorporated into the sol-gel mixture for identifying bacterial antibiotic resistance. It may be appreciated that the emission of fluorescence from bacteria in spite of the presence of a specific antibiotic, indicates that said bacteria is antibiotic-resistant. Partial resistance may be indicated when the presence of the specific antibiotic leads to a partial reduction in the number of fluorescent bacteria. The following antibiotics are added to the sol-gel mixture: Chloramphenicol, Erythromycin, Tetracycline, Streptomycin, Polymyxin, Nalidixic Acid, Novobyocin, Trimethoprin, Rifanapicin and Penicillin.

According to the present invention, it is possible to provide the markers as liposomes; films; multilayers; braided, lamellar, helical, tubular, and fiber-like shapes; solvated rods; solvated coils; and combinations thereof. According to the present invention, it is also possible to detect injured or stressed microorganisms by incorporating pyruvate or $K_2SO_4$ within the sol-gel. It is known in the art that pyruvate or $K_2SO_4$ can be used to resuscitate or improve chlorinated injured coliform bacteria ("enumeration and differentiation of chlorine-stressed total coliform bacteria" Robert A Duncanson—Ph.D. dissertation—University of Rhode Island 1993).

According to the present invention it is possible to add polylysine or similar substances at a concentration of between 10 to 100 parts per million to the sol-gel solution to allow for enhancing bacteria absorption.

All the above and other characteristics and advantages of the invention will be further understood from the following illustrative and non-limitative examples of preferred embodiments thereof.

DETAILED DESCRIPTION OF PREFERRED EMBODIMENTS

Figure 1:
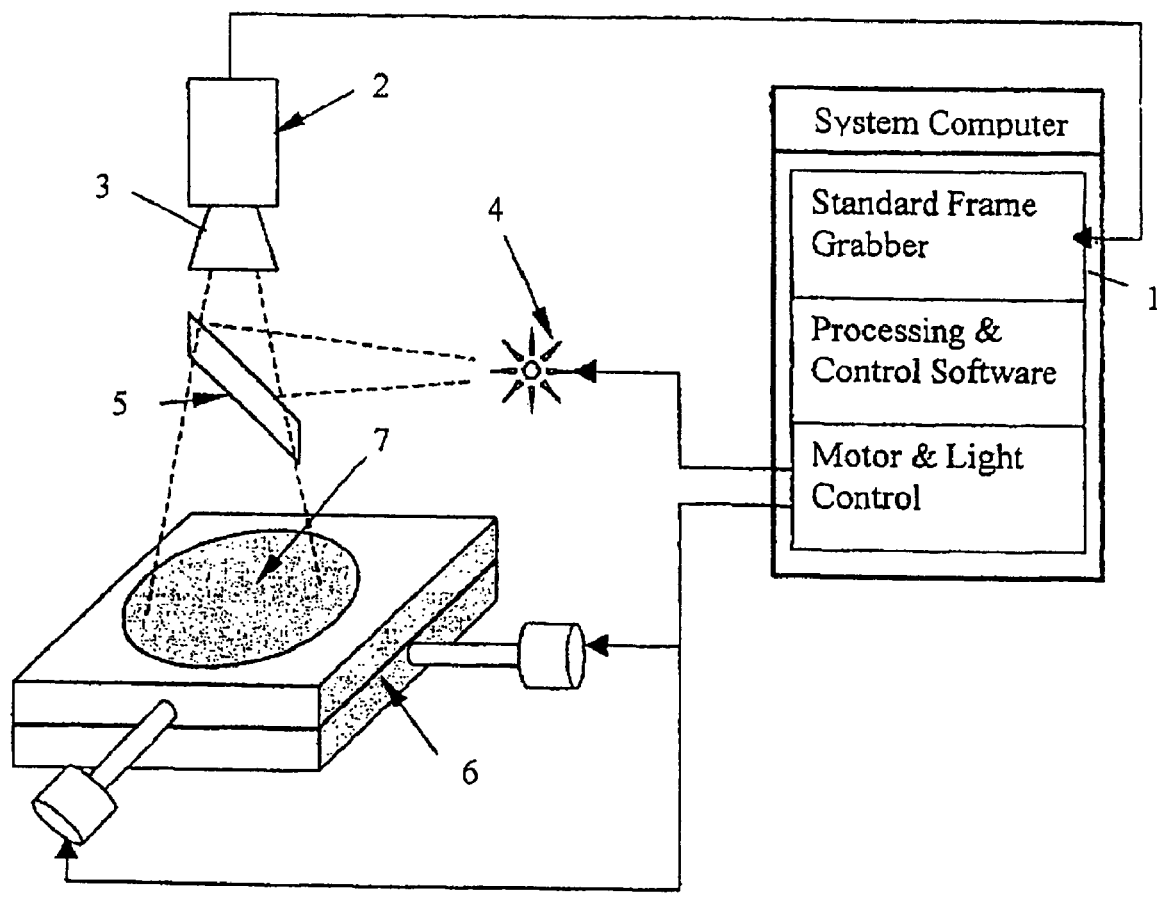
FIG. 1 illustrates a system for identifying and enumerating microorganisms, according to a preferred embodiment of the invention.

According to a preferred embodiment, the system for enumeration of bacteria comprises the following components shown in FIG. 1: standard frame grabber coupled with a computer, processing and controlling software, and motor and light control apparatus—collectively indicated at (1), standard CCD array camera with frame rate of 30 fps and frame dimensions of 640×480 (2), an epi-fluorescence or fluorescence microscope with a 400 and/or 1000 magnification and with an autofocus system (3), a light source (4), a beam splitter (5), a mechanical x-y table (6) on which a filter (7) is placed.

In another preferred embodiment of the invention, instead of utilizing a standard CCD system, a CCD Line Approach is used comprising a CCD line camera, Line dimension: 512 pixels, Line rate: 70 kHz equivalent to 135 frames of 512×512 $pixel^2$ per second, Custom-design signal synchronization hardware, Custom-design digital/analog signal processing hardware For the purpose of clarity, and as an aid in the understanding of the invention, as disclosed and claimed herein, the following abbreviations are defined below:
CFU—colony forming unit.
MUG—4-methylumbelliferyl β-D-galactopyranoside
FDG—fluorescein di-β-D-galactopyranoside
CUG—3-carboxyumbelliferyl β-D-galctopyranoside

EXAMPLE 1

Preparation of Sol-Gel-Coated Glass Slides

Standard microscope slides were washed in soap water by gentle shaking for 30 minutes, and were then initially rinsed with tap water, followed by an additional rinse with tri-distilled water. The slides were then dried over night in an incubator at (36° C.). The cleansed microscopic slides were then stored in soft paper for further use.

A typical starting solution for the thin sol-gel film preparation was as follows: 0.9 ml pure pyridine+0.2 ml CUG solution (100 mM)+0.1 ml $H_2O$ were stirred for 1 minute (with a small magnet). If the substrate did not completely dissolve only the upper phase of the mixture was used. 0.8 ml of the above mentioned solution were mixed with 0.4 ml of methyltrimethoxy silane (MTMS, Fluka). The whole solution was well mixed by magnetic stirrer for additional 2 minutes. For reaction initiation, 30 μl of HCl 0.1 M were added to the above solution, followed by 5 minutes magnetic stirring.

The slides were then coated with 40 μl of the resulting solution by using a fine pipette. The solution was spread equally along the glass by means of a spin coating. The coated glass was dried in darkness for a period of 24 hours under dry conditions and at room temperatures. After the initial drying period, the sol-gel-coated slides were wrapped with aluminium foil and stored in a cool place.

EXAMPLE 2

Example 1 was repeated, using a 0.1 ml solution of 4'-6-diamino-2-phenyl indole at a 0.016 mg/ml concentration. The results obtained was similar to that of Example 1.

EXAMPLE 3

*E. coli* Identification and Enumeration

An *E. coli* bacteria culture was grown in a nutrient broth for 24 hours at 36° C. A seeded solution of bacteria with an estimated concentration of $10^8$ bacteria/ml was prepared in sterile distilled water. A series of different solutions was prepared (350 ml of each solution) with an anticipated bacteria concentration as follows: $10^9$ bacteria in 100 ml, $10^8$ bacteria in 100 ml, $10^7$ bacteria in 100 ml, $10^6$ bacteria in 100 ml $10^5$ bacteria in 100 ml.

All bacteria concentrations were verified by performing parallel membrane filtration (MF) test in water samples. This was done by diluting the solution with sterile distilled water in sterile plastic bottles so that a dilution of up to $1:10^8$ was accurately achieved.

In order to count the bacteria in a given sample the water sample was first filtered through a Millipore filter (0.47 μm, 13 mm). The Millipore filter was then placed upside down on the sol-gel surface. In order to create full contact with the filter and the sol-gel, a minute quantity of sterile water (10 μl) was placed over the filter surface and pressure (up to 0.5 kg/cm$^2$) was applied.

The bacteria were then incubated together with the sol-gel for a period of 2.0 hours at 36° C. in a humid container (consisting of a large petri dish with a moist Wattman pad, in order to prevent the filter from drying and breaking away from the sol-gel). The Millipore filter was then discarded and the slide was dried during 10-15 minutes at 44.5° C.

For the purpose of enumerating the bacteria, the sol-gel slide was viewed under a microscope system (Zeiss Axiolab with an epiflourescence illumination system and a 50 W mercury lamp) with a magnification of ×400 that utilizes a LP420 filter. In order to eliminate natural fluorescent algae which may create false positive results, specific light wavelengths were used (e.g., a LP420 filter).

Figure 2:
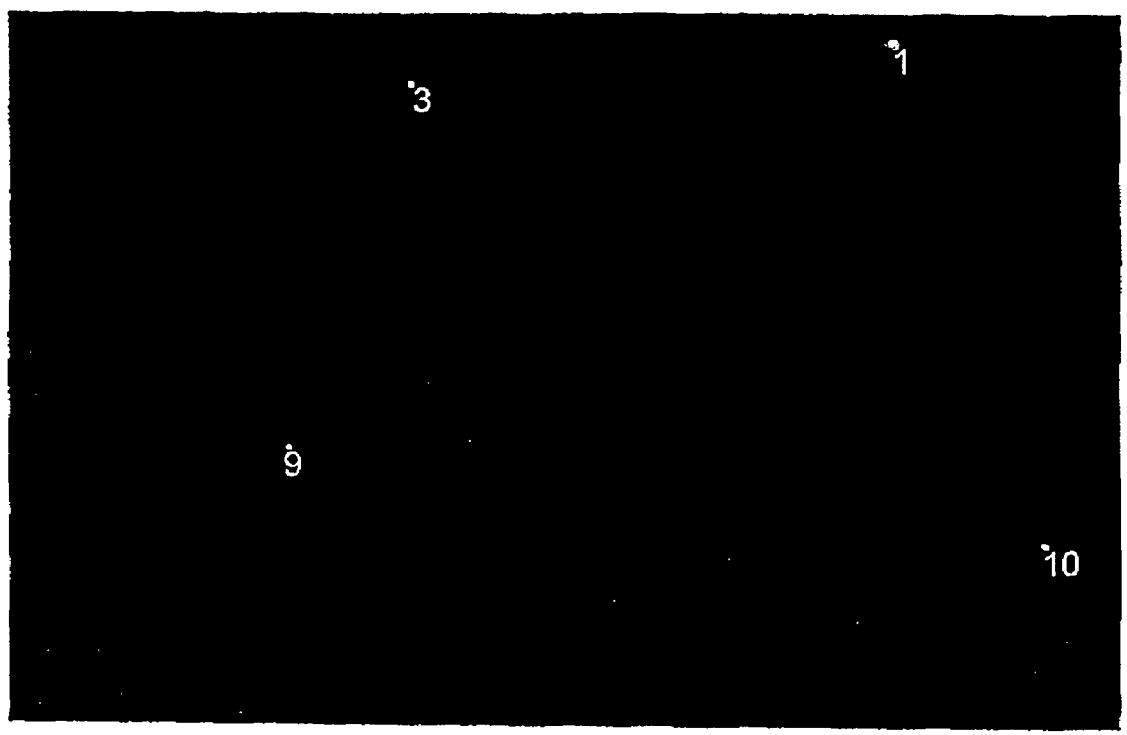
FIG. 2 is a fluorescence picture of *E. coli* bacteria on a sol-gel surface at ×400 magnification.

Pictures of the fluorescent spots were taken at 5 various random locations on the sol-gel-coated slide. FIG. 2 is a picture taken at 400 magnification of *E. coli* bacteria on a sol-gel surface. The number of fluorescence spots were then counted by using image processing software (Image-Pro Plus, Media Cybernetics). The number of counts obtained following the analysis is indicated in Table I.

TABLE I

| Test Number | Initial Coliform Count (CFU/1 ml) | Picture Number | Number of Fluorescent Spots Counted (Units) | Estimated Number of Bacteria (CFU/1 ml) | Average Number of Bacteria (CFU/1 ml) |
|---|---|---|---|---|---|
| 1 | $10^6$ | 1 | 550 | 980,000 | 1,014,000 |
|   |   | 2 | 500 | 890,000 |   |
|   |   | 3 | 600 | 1,070,000 |   |
|   |   | 4 | 575 | 1,020,000 |   |
|   |   | 5 | 625 | 1,110,000 |   |
| 2 | $10^5$ | 1 | 57 | 83,000 | 96,800 |
|   |   | 2 | 56 | 99,000 |   |
|   |   | 3 | 50 | 89,000 |   |
|   |   | 4 | 58 | 103,000 |   |
|   |   | 5 | 62 | 110,000 |   |
| 3 | $10^4$ | 1 | 5 | 8,900 | 9,600 |
|   |   | 2 | 6 | 10,700 |   |
|   |   | 3 | 8 | 14,200 |   |
|   |   | 4 | 5 | 8,900 |   |
|   |   | 5 | 3 | 5,300 |   |

Since the area of vision of the microscope was known, the number of fluorescent spots counted in each slide gives an exact estimate of the initial amount of bacteria that was in the original solutions.

EXAMPLE 4

Description of Algorithm to Enumerate the Number of Fluorescence Spots Using Image-Pro Plus The algorithm described here is an example used for detecting and enumerating bacteria on sol-gel images. The purpose of this algorithm is to detect bright spots with the expected size: Low-pass filtering was used for high frequency noise reduction. Image segmentation was used leading to a binary image of white blobs of bacteria on black background. The segmentation in this implementation was done using a simple threshold application, with a constant pre-defined threshold.

The analysis comprises the following steps:
A) Binary image labeling, resulting in a list of blob objects, candidates for being indicated as bacteria.
B) Geometry features calculation of the blob list elements (area, contrast, etc.).
C) Elimination of candidates of which size and contrast are outside the expected range.
D) Enumeration of the candidates left after the geometrical filtering.

Figure 3:
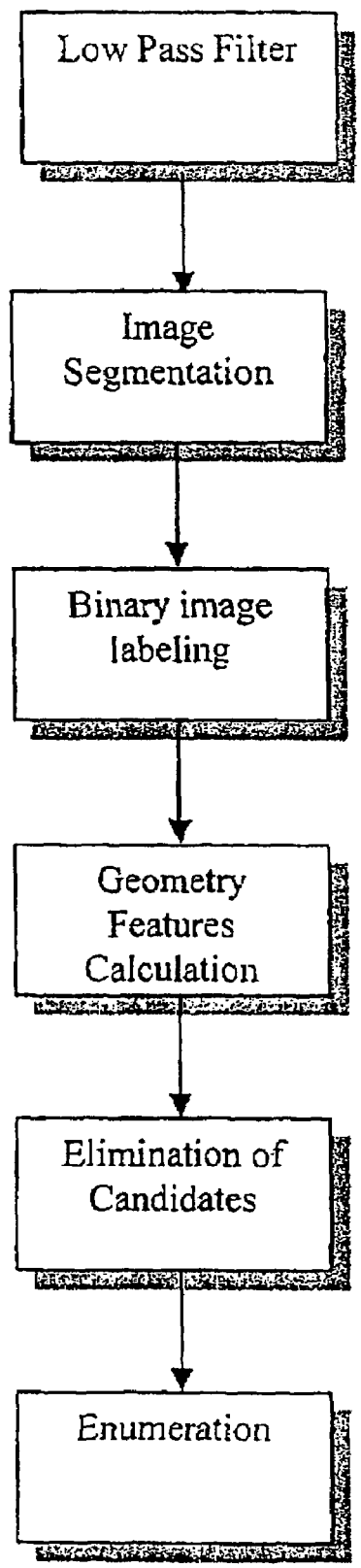
FIG. 3 is a flow-chart of a process according to a preferred embodiment of the invention.

An example script of the above algorithm is shown in FIG. 3, which illustrates a process comprising the following stages:

Stage 1: Low-pass filtering for high frequency noise reduction.
Stage 2: Image segmentation that results in a binary image of white blobs of bacteria on black background. The segmentation in this implementation is done using a simple threshold application, with a constant pre-defined threshold. If necessary, an automatic and/or dynamic threshold calculation can be used.
Stage 3: Binary image labeling, resulting in a list of blob objects, candidates for being indicated as bacteria.
Stage 4: Geometry features calculation of the blob list elements (area, contrast, etc.).

Stage 5: Elimination of candidates the size and contrast of which are outside the expected range.

Stage 6: Enumeration of the candidates left after the geometrical filtering.

While specific embodiments of the invention have been described for the purpose of illustration, it will be understood that the invention may be carried out in practice by skilled persons with many modifications, variations and adaptations, without departing from its spirit or exceeding the scope of the claims.

The invention claimed is:

1. A method for detecting and enumerating viable microorganisms in a sample, providing a reliable direct count of individual viable microorganisms contained in the sample, comprising:
   providing a smooth transparent porous material composed of sol-gel and containing a marker in pores thereof;
   separating the microorganisms from a sample to be analyzed and contacting the microorganisms with the smooth transparent porous material, thereby transferring the separated microorganisms to a surface of the smooth transparent porous sol-gel material;
   incubating the contacted microorganisms and smooth transparent porous marker containing sol-gel material for a time sufficient to update the marker from the pores, to promote uptake of the marker by viable microorganisms;
   irradiating the marker containing smooth transparent porous sol-gel material with an energy source to generate detectable signals emitted by the marker taken up by the viable microorganisms, and
   detecting the signals emitted and analyzing the signals to identify and enumerate the viable microorganisms.

2. A method according to claim 1 wherein the microorganisms are bacteria.

3. A method according to claim 1 wherein the energy source is selected from the group consisting of visible light, fluorescent light, UV light, infrared light, an electro-magnetic field, sonar, ultrasonic waves, radio waves, and short wave radiation.

4. A method according to claim 1, further comprising isolating the microorganisms from a sample selected from the group consisting of water, milk, food, saliva, urine, throat swab tests, wounds, sputum, stomach content, and feces.

5. The method according to claim 1, wherein the marker is selected from the group consisting of 3-carboxyumbelliferyl β-D-galactopyranoside, 4-chloromethyl-6,8-difluoroumbelliferyl β-D-galactopyranoside, 4-methylumbelliferyl β-D-galactopyranoside, fluorescein di β-D-galactopyranoside, 6,8-difluoroumbelliferyl β-D-glucuronide, 5-(pentafluorobenzoylamino) fluorescein di-β-D-glucuronide, and β-trifluoromethylumbelliferyl β-D-glucuronide.

6. The method according to claim 1 further comprising attaching antibiotic substances to the marker.

7. The method according to claim 6, wherein the antibiotic substance is selected from the group consisting of Chloramphenicol, Lrythromycin, Tetracycline, Streptomycin, Polymyxin, Nalidixic Acid, Novobyocin, Trimethorprin, Rifanapicin and Penicillin.

8. The method according to claim 1, wherein the markers are provided in a form selected from the group consisting of liposomes; films; multilayers; braided; lamellar, helical, tubular, and fiber shapes; solvated rods; solvated coils; and combination thereof.

9. The method according to claim 1, farther comprising providing pyridine or $K_2SO_4$ in the smooth transparent porous material.

10. The method according to claim 1, further comprising detecting microorganisms present at less than $10^3$ ml$^{-1}$.

11. The method according to claim 1, wherein separating the microorganisms from a sample comprises filtering the sample to capture microorganisms on a filter media, and placing the filter media in contact with the smooth transparent porous material containing the marker.

12. The method of claim 11 further comprising co-incubating the filter media with the smooth transparent porous material.

13. The method of claim 12 wherein the co-incubating is conducted at 0.5 to 6 hours at a temperature of between 35 and 44° C.

14. A system for identifying and enumerating viable microorganisms in a sample, the system being sufficiently sensitive to provide a reliable direct count of individual viable microorganisms contained in the sample comprising;
   a smooth transparent porous material composed of sol-gel and containing at least one marker in the pores therein;
   separation means for separating the microorganisms from a sample to be analyzed, the separated microorganisms transferred to a surface of the smooth transparent porous sol-gel material, such that the microorganisms contact the marker contained thereon;
   means for incubating the microorganisms with the marker-containing smooth transparent porous material such that the marker is uptaken from the pores, the viable microorganisms ingest the marker and metabolize the marker for emitting detectable signals from the viable microorganisms;
   means for irradiating the marker ingested by the viable microorganisms disposed on the marker-containing smooth transparent porous material for generating the detectable signals emitted by the marker;
   means for detecting the signals; and
   means for analyzing the detected signals to identify and enumerate the viable microorganisms.

15. The system of claim 14, wherein the irradiating means comprise an energy source selected from the group consisting of visible light, fluorescent light, UV light, infrared light, an electrochemical field, sonar, ultrasonic waves, radio waves and short wave radiation.

16. The system of claim 14, wherein the detecting means comprise a frame grabber, a CCD array camera, a microscope, and an autofocus system.

17. The system of claim 14, further comprising a mechanical x-y table.

18. The system of claim 16, wherein the frame grabber has a rate of 30 frames per second.

19. The system according to claim 14 wherein the microorganisms are bacteria.

20. The system according to claim 14 wherein the sample is selected from the group consisting of water, milk, food, saliva, urine, throat swab tests, wounds, sputum, stomach content, and feces.

21. The system according to claim 14 wherein the marker is selected from the group consisting of 3-carboxyumbelliferyl β-D-galactopyranoside, 4-chloromethyl-6,8-difluoroumbelliferyl β-D-galactopyranoside, 4-methylumbelliferyl β-D-galactopyranoside, fluorescein di β-D-galactopyranoside, 6,8-difluoroumbelliferyl β-D-glucuronide, 5-(pentafluorobenzoylamino) fluorescein di-β-D-glucuronide, and β-trifluoromethylumbelliferyl β-D-glucuronide.

22. The system according to claim 14 wherein the marker has at least one antibiotic substance attached thereto.

23. The system according to claim 22, wherein the antibiotic substance is selected from the group consisting of Chloramphenicol, Lrythromycin, Tetracycline, Streptomycin, Polymyxin, Nalidixic Acid, Novobyocin, Trimethorprin, Rifanapicin and Penicillin.

24. The System according to claim 14, wherein the marker is in a form selected from the group consisting of liposomes; films; multilayers; braided; lamellar, helical, tubular, and fiber shapes; solvated rods; solvated coils; and combination thereof.

25. The system according to claim 14 wherein the smooth transparent porous material contains pyridine or $K_2SO_4$.

26. The system according to claim 14 wherein the system detects microorganisms present at less than $10^3$ ml$^{-1}$.

27. The system according to claim 14 wherein the separation means comprise a filter for filtering the sample to capture microorganisms on a filter media, the filter media contacted with the smooth transparent porous material containing the marker.

28. The system of claim 27 wherein the filter media is co-incubated with the smooth transparent porous material.

29. The system of claim 28 wherein the filter media is co-incubated with the smooth transparent porous material for 0.5 to 6 hours at a temperature of between 35 and 44° C.

30. The system of claim 14 wherein the smooth transparent marker containing sol-gel material is a smooth transparent marker containing sol-gel coating supported on a slide.

* * * * *